US005279596A

United States Patent [19]

Castaneda et al.

[11] Patent Number: 5,279,596

[45] Date of Patent: Jan. 18, 1994

[54] INTRAVASCULAR CATHETER WITH KINK RESISTANT TIP

[75] Inventors: Javier E. Castaneda; Robert F. Graham; Peter Soltesz; Thomas Trotta, all of Miami, Fla.

[73] Assignee: Cordis Corporation, Miami Lakes, Fla.

[21] Appl. No.: 905,491

[22] Filed: Jun. 25, 1992

Related U.S. Application Data

[63] Continuation of Ser. No. 559,193, Jul. 27, 1990, abandoned.

[51] Int. Cl.⁵ .............................. A61M 25/00

[52] U.S. Cl. .............................. 604/282; 138/133; 128/658; 604/280

[58] Field of Search .............................. 604/280-283; 264, 93, 606/191, 192, 194; 128/4-6; 657, 658, 772; 138/123, 127, 129, 133, 138, 174

[56] References Cited

U.S. PATENT DOCUMENTS 3,426,744 2/1969 Ball .
3,618,613 11/1971 Schulte .
3,890,976 6/1975 Bazell et al. .............. 604/96
3,924,632 12/1975 Cook .............. 604/282
4,044,765 8/1977 Kline .
4,430,083 2/1984 Ganz et al. .............. 604/265
4,498,473 2/1985 Gereg .
4,516,972 5/1985 Samson .............. 604/282
4,531,943 6/1985 Van Tassel et al. .............. 604/96
4,577,543 3/1986 Wilson .............. 604/280
4,610,674 9/1986 Suzuki et al. .
4,634,432 1/1987 Kocak .
4,665,604 5/1987 Dubowik .
4,705,511 11/1987 Kocak .
4,737,153 4/1988 Shimamura et al. .............. 604/282
4,817,613 4/1989 Jaraczewski et al. .............. 128/658
4,842,590 6/1989 Tanabe et al. .............. 604/282
4,886,506 12/1989 Lovgren et al. .............. 604/280
4,899,787 2/1990 Ouchi et al. .............. 138/131
4,955,862 12/1990 Sepetka .............. 128/658

*Primary Examiner*—C. Fred Rosenbaum
*Assistant Examiner*—Chalin Smith
*Attorney, Agent, or Firm*—Gerstman & Ellis, Ltd.

[57] ABSTRACT

An intravascular catheter comprises a proximal portion and a distal portion. The proximal portion has greater torsional stiffness than the distal portion, while the distal portion has greater dependability than the proximal portion. In accordance with this invention the distal portion carries a helical wire support member embedded therein, the helical support member being essentially free of crossing wires, to provide kink-resistance upon bending to the distal portion.

24 Claims, 1 Drawing Sheet

14 22 28 24 32
28 28 26

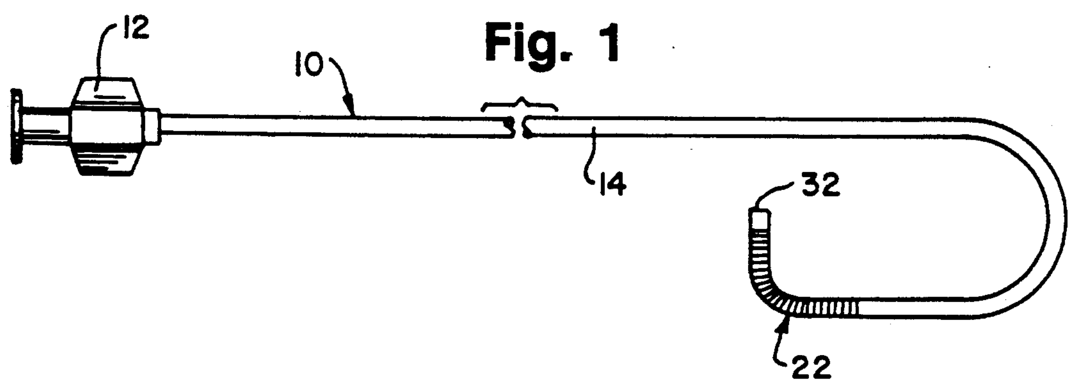
Fig. 1
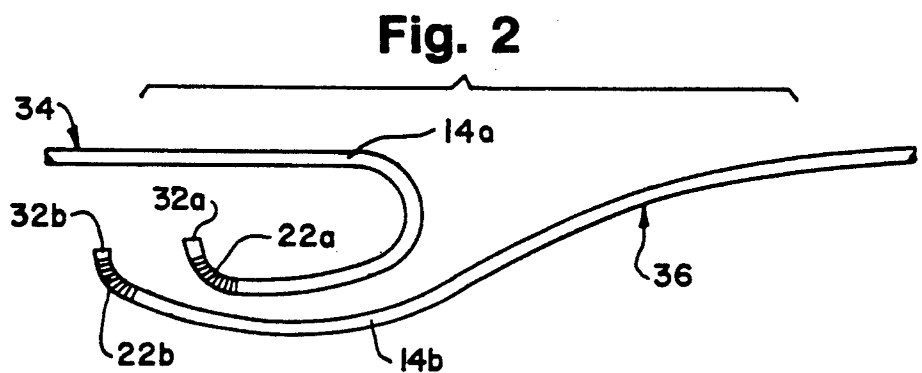
Fig. 2
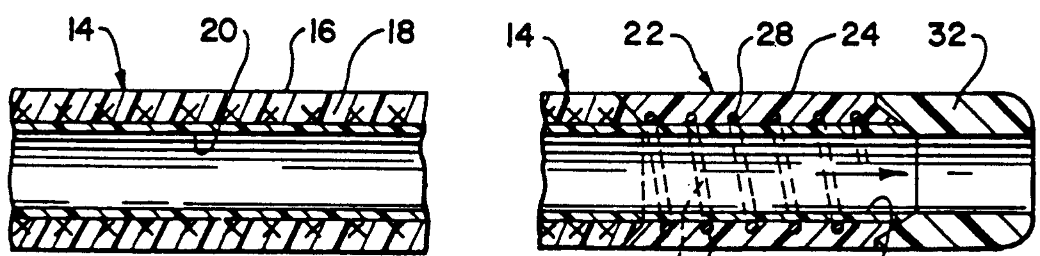
Fig. 3
Fig. 4
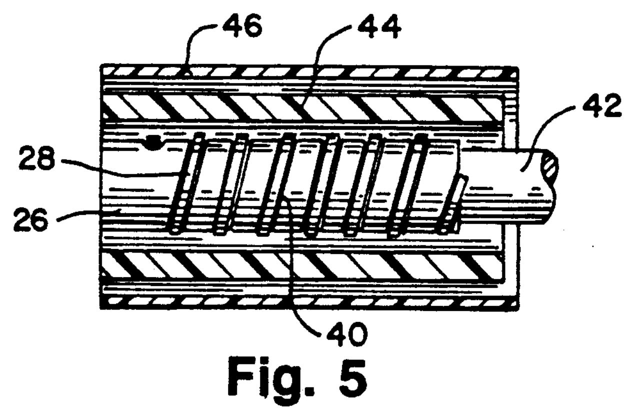
Fig. 5

INTRAVASCULAR CATHETER WITH KINK RESISTANT TIP

This is a continuation of application Ser. No. 559,193 filed Jul. 27, 1990 now abandoned.

BACKGROUND OF THE INVENTION

This invention relates to an intravascular catheter which exhibits improved resistance to kinking in the tip even when the tip is thin-walled and flexible.

Intravascular, and particularly intravascular catheters for angioplasty or angiography are equipped with a pliable tip to facilitate the advancement of the catheter through the vascular system of a patient toward its objective, typically a coronary artery or a chamber of the heart. The proximal majority of the catheter length is typically flexible but firm, being generally equipped with a tubular, braided or otherwise crossing wire reinforcement member to provide torsional stiffness and pushability to the catheter. Thus the catheter may be reliably rotated from the proximal end to cause the distal end to rotate a substantially equal amount.

However, the distal tip end of the catheter is desirably more flexible than is generally possible with such a tubular braid-reinforced catheter section. Accordingly, in the prior art most catheters of this type carry no wire reinforcement at all at the distal tip.

Because of this, a problem arises in that, while the distal tip portions of prior art catheters are adequately flexible and soft so that advancement of the catheter does not injure vascular or heart tissues, the tip portion is subject to collapsing or kinking when it is directed around a bend in a branched blood vessel or the like. This of course is deemed undesirable, even if the plastic material of the tip portion is capable of springing back into uncollapsed condition when it is straightened out again.

Accordingly, there is a need for a catheter which has a high torsion resistance in its proximal section in accordance with the prior art, but which exhibits a highly flexible tip which, nevertheless, has substantial collapse resistance, particularly resistance against kinking as the tip is directed about a bend in a blood vessel.

In accordance with this invention, a catheter is provided which has a distal portion which may be soft and pliable as needed, but in which the distal portion is strongly resistant to collapse so that it may be directed through a labyrinth of branching blood vessels or the like without damaging tissues, but without collapsing or kinking. The resulting catheter exhibits improved characteristics over prior art catheters, particularly for the well-known PTCA procedure or any other angioplasty or angiography procedure.

As a further advantage, the plastic material out of which the distal portion of the catheter of this invention can be made may be inherently softer than in the prior art, for added tolerability of catheter advancement through tissues. At the same time, the distal section exhibits its improved and desired resistance to collapse or kinking.

DESCRIPTION OF THE INVENTION

In this invention, an intravascular catheter is provided which comprises a proximal portion and a distal portion. The proximal portion has greater torsional stiffness than the distal portion. The distal portion has greater bendability than the proximal portion.

In accordance with this invention, the distal portion carries a helical wire support member embedded therein, which support member is essentially free of crossing wires. Thus, kink resistance is provided to the distal portion upon bending thereof, but the distal portion remains soft and flexible.

Preferably, the helical support member may be completely embedded in the catheter distal portion in a manner which is analogous to prior art structures, where complete embedding of braided wire support tubes is provided.

It is preferred for the proximal catheter portion to carry a braided wire tubular support member embedded therein, to provide the desired torsional stiffness to the catheter. The distal catheter portion of this invention is typically a relatively minor portion of the overall length of the catheter, being found primarily adjacent the tip thereof. Typically, the distal catheter portion is less than one-tenth the length of the overall catheter, and often only about two or three percent of the overall catheter length.

The embedded coils of the helical support member are preferably spaced from one another so that plastic material of the distal portion isolates each of the coils from each other. This provides an improved flexibility to the distal catheter portion, coupled with a good softness which can be provided by the use of a plastic material that is typically softer than the plastic material of prior art catheter distal portions. Generally, it is preferred for the distal catheter portion plastic material to have a Shore "D" durometer of 25 to 50, and preferably 35 to 45, compared with a similar durometer of prior art catheter tips of 60 or more. This can be accomplished because of the reinforcing capability of the helical support member, so that a softer plastic material ma be used in the distal catheter portion, while at the same time the distal catheter portion remains highly resistant to collapse and kinking.

The distal catheter portion may carry a distal tip that is free of supporting strands. Typically, such a distal tip is a relatively short stub, typically less than 1 cm. in length, and may carry a relatively high concentration of x-ray contrast medium to facilitate the x-ray visibility of the catheter of this invention.

DESCRIPTION OF THE DRAWINGS

In the drawings, FIG. 1 is a plan view of an intravascular catheter in accordance with this invention;

FIG. 2 is a fragmentary, plan view of a pair of coronary catheters in accordance with this invention, showing differing designs of preformed curves in their distal ends;

FIG. 3 is a longitudinal sectional view of part of the proximal portion of a catheter of FIG. 1;

FIG. 4 is a longitudinal sectional view of the distal portion of a catheter of FIG. 1 in accordance with this invention, in straightened form; and FIG. 5 is a longitudinal sectional view of a step of one manufacturing process of the catheter of this invention.

DESCRIPTION OF SPECIFIC EMBODIMENTS

Referring to FIG. 1, a plan view of a catheter in accordance with this invention is disclosed. Catheter 10 defines a proximal hub 12 which may be of conventional design, connected with a proximal portion 14, which comprises the majority of the length of catheter 10 and may be about 38 inches long. As shown in FIG. 3, proximal portion 14 may comprise coaxial, extruded layers including an outer layer 16 which may be made of polyurethane, nylon, or the like, and a central layer 18 which includes embedded tubular woven wire braiding of conventional design for catheters, with the nylon or other compatible plastic material permeating the interstices of the tubular braiding in conventional manner. Layers 16, 18 may be a single extrusion. Finally, an innermost layer 20 of polytetrafluoroethylene may be provided.

Typically, the catheter of claim 1 may be sized to penetrate the smaller coronary arteries for use as a guiding catheter. Inner layer 20 may be 0.0015 inch thick, while the tubular, braided layer 18 and outer layer 16 may have a thickness of 0.004 inch. The entire catheter may be about 100 centimeters in length, having an outer diameter of about 0.092 inch and an inner diameter of about 0.072 inch.

Catheter 10 also defines a distal portion 22, conventionally bonded to the distal end of proximal portion 14 and typically of the same outer diameter. A portion of distal portion 22 is shown in longitudinal section in FIG. 4, in which it can be seen that distal portion 22 comprises inner and outer coaxially positioned tubular sections. Outer tubular section 24 may be of the same outer diameter as proximal section 14, being made of nylon or the like. Inner tubular section 26 may be similar to inner tubular section 2 of the proximal section, being made of polytetrafluoroethylene, and also being of similar transverse dimensions thereto.

Outer tubular section 24 carries a helical wire support member 28, which is completely embedded within distal portion 22, as shown, with the various embedded coils of helical wire support member being spaced from each other as also shown, being separated by the plastic material of tubular section 24 such as nylon or other compatible plastic material. The wire of helical wire support member 28 may be of normally round cross section, but, preferably, it is of rectangular cross section of greater width than height. This provides a strong coil while reducing the radial depth (i.e., the thickness) of the wire cross section which, in turn, reduces the chances that the wire can be exposed to the exterior at the outer surface of distal catheter portion 22. For example, the helical wire may have a cross section of 0.002 inch in height, which will be the radial direction, and 0.006 inch in width. Such a wire may be completely encapsulated in the wall of distal catheter portion 22, even when the overall wall thickness is only about 0.01 inch.

Distal portion 22, which is typically substantially about 2½ percent of the length of proximal catheter portion 14, and is about one inch in length. Catheter portion 22 exhibits a substantially increased softness and resilience when compared with the softness and resilience of proximal section 14. This is particularly provided by the fact that the helical supporting wire 28 permits distal portion 22 to be twisted with significantly reduced torsion resistance when compared with the majority of the catheter in proximal portion 14. Also, the plastic material that makes up outer tubular section 24 and surrounds and impregnates the helical wire 28 may be softer than plastics that are normally used in catheters, even at their tips, being of a Shore D durometer of about 40. This is contrary to a typical plastic material used in conventional catheters at the tip which have a Shore D durometer on the order of 62. This substantially increased softness of the plastic material used in distal catheter portion 22 provides a portion that is very soft, resilient, and undamaging to tissues as the catheter is advanced through the cardiovascular system of a patient. At the same time, the presence of supporting helical wire 28 provides an underlying strength and stability to distal portion 22 along with the softness and resilience, particularly so that the soft distal portion 22 is greatly resistant to kinking as it is distorted out of its normal, unstressed configuration as shown in FIG. 1 by the action of being forced through a convoluted, highly branched blood vessel system or the like. Distal portion 22 is free of crossing wires, which would reduce its soft, pliable characteristic.

Additionally, distal catheter portion 22 can carry a tubular distal tip 32, bonded to the remainder of distal portion 22, which is free of any form of wire reinforcement. The length of such a tip may be about 0.1 cm., and may be similar to the commercially available BRITE TIP (T.M.) catheter tip provided to many catheters which are marketed by the Cordis Corporation. The plastic material of catheter tip 32 contains a relatively high loading of radiopaque agent, for increased x-ray visibility of catheter tip 32.

The various components of the catheters of this invention may be conventionally bonded together in accordance with the known principles of catheter design and manufacture.

Turning to FIG. 2, a pair of coronary catheters are shown, making use of the invention of this application, the catheters being in their natural, unstressed configuration. Catheter 34 illustrates a desired shape for a left coronary catheter, with proximal portion **14*a* and distal portion 22 being of a construction similar to that previously described. Catheter 36 illustrates a desired shape for a right coronary catheter, with proximal portion 14*b* and distal portion 22*b* being of similar design to the above as well. Both catheters may carry tips 32*a* and 32*b* of a design similar to tip 32** of the previous embodiment. These catheter shapes facilitate engagement by their respective distal tips to the coronary ostium and attain the proper take off angle to provide better alignment of the catheter and artery. This can facilitate passage of PTCA catheters which extend through the lumen of the catheters of this invention and are thus properly guided into the proper location therethrough, as one possible use of the catheter of this invention. Alternatively, the catheter of this invention may be used in its own right for angiography or angioplasty.

Referring to FIG. 5, a method for the manufacture of the distal catheter portion 22 is disclosed.

Using a coil winder with accurate tension and pitch control, stainless steel wire is coiled into the helical wire support member 28, to be provided to distal portion 22 in accordance with this invention. Helical wire 28 is placed about preformed polytetrafluoroethylene tubular layer 26, and both are placed about pin 42. Optionally, helical member 28 may fit into optional helical groove 40 of pin 42. Alternatively, the pin 42 may be cylindrical. The size of pin 42 may be selected so that the helically coiled wire 28, after winding, springs back into a relaxed position that is the desired diameter of helical wire 28 in distal catheter portion 22. Preferably, wire 28 is made of high tensile strength spring steel.

Accordingly, coil 28 on the pin 42 may optionally be considerably smaller than the desired, relaxed inside diameter of the coil 28 as placed into catheter section 22. For example, to make a coil of desired unstressed diameter of 0.08 inch, one may typically use a pin 42 having a diameter of about 0.05 inch, although this depends on the cross-sectional dimensions of the coiled wire, its hardness, its coiling tension, and the like. Then, after release of the coil, it springs back outwardly into the desired final dimension.

After wire 28 and tube 26 has been applied to pin 42, oversized plastic sleeve 44 is applied, which is intended to become the plastic portions 16, 18 of outer tubular portion 24. Wire coil 28 may be applied to pin 42 under tension to keep it to the size of the pin, typically by a screwing action to wind the coil 28 into the grooves 40. Plastic sleeve 44 is assembled over the coil, and a heat shrink tubing 46 (made for example of polytetrafluoroethylene) is applied about plastic sleeve 44. Then, the assembly is heated at a temperature at or above the softening point of plastic sleeve 44, which causes heat shrink tubing 46 to press tubing 44 forcefully against coil 28 and tube 26, and for the plastic of tubing 44 to encapsulate the coils of helical wire 28.

After the system has once again cooled, the shrink tubing 46 can be removed by longitudinal slicing, and the composite of tubing 44, coiled wire 30, and tubing 26 can be removed by an unscrewing action from the pin 42.

Following this, the resulting product, which constitutes distal catheter portion 22, may be attached to proximal portion 14 by conventional bonding, as a step of manufacture of the overall catheter. To obtain the best possible outer diameter control of outer tubular portion 24, that portion may be ground by a centerless grinding means after the step of fusing plastic tubing 44 and helical wire 2 together.

Thus, by this means, a catheter is provided, typically for intravascular use, in which the proximal portion has greater torsional stiffness than the distal portion, but the distal portion has greater bendability than the proximal portion and exhibits good kink resistance upon bending of the distal portion. Additionally, the distal portion may be very soft and flexible despite its kink resistance, so that such a catheter is easily advanceable through a labyrinth of blood vessels with greater ease but without damage to tissues.

The above has been offered for illustrative purposes only, and is not intended to limit the scope of the invention of this application, which is as defined in the claims below.

We claim:

1. An intravascular catheter which comprises a proximal portion and a distal portion, said proximal portion having greater torsional stiffness than said distal portion, said distal portion having greater bendability than said proximal portion, the improvement comprising, in combination:
   said distal portion defining a smooth-walled lumen and carrying a helical wire support member embedded therein, said helical support member being essentially free of cross wires, to provide kink-resistance upon bending to said distal portion, said proximal portion carrying a braided wire tubular support member embedded therein, said catheter defining an inner, lumen-defining tubular plastic layer positioned radially within said helical support member and a braided wire tubular support member.

2. The catheter of claim 1 in which said distal catheter portion is less than one-tenth the length of said proximal catheter portion.

3. The catheter of claim 1 in which said distal catheter portion carries a distal tip that is free of supporting strands.

4. The catheter of claim 1 in which said helical support member defines embedded coils that are spaced from each other.

5. The catheter of claim 1 in which said distal catheter portion defines a preformed bend.

6. The catheter of claim 1 in which said distal catheter portion comprises a plastic material that is softer than the plastic material of the proximal catheter portion, said distal catheter portion plastic material having a Shore "D" durometer of 25 to 50.

7. The catheter of claim 1 in which the wire of said helical support member defines a rectangular cross section, with the width of said wire being greater than the radial depth thereof.

8. An intravascular catheter which comprises a proximal portion and a distal portion, said proximal portion having greater torsional stiffness than said distal portion and carrying a braided wire tubular support member embedded therein, said distal portion having greater bendability than said proximal portion, the improvement comprising, in combination:
   said distal portion carrying a helical wire support member completely embedded therein, said helical support member being essentially free of crossing wires, to provide kink-resistance upon being to said distal portion, the length of said distal portion being less than one tenth the length of said proximal portion.

9. The catheter of claim 8 in which said helical support member defines embedded coils that are spaced from each other.

10. The catheter of claim 9 in which said distal catheter portion comprises a plastic material that is softer than the plastic material of the proximal catheter proportion, said distal catheter portion plastic material having a Shore D durometer of 35 to 45.

11. The catheter of claim 10 in which said distal catheter portion defines a preformed bend.

12. The catheter of claim 11 in which said distal catheter portion carries a distal tip that is free of supporting strands.

13. The catheter of claim 8 in which the wire of said helical support member defines a rectangular cross section, with the width of said wire being greater than the radial depth thereof.

14. An intravascular catheter which comprises:
   an elongated tube having a proximal portion and a distal portion;
   said proximal portion extending most of the length of the catheter and having a greater torsional stiffness than said distal portion;
   said distal portion defining a smooth-walled lumen and having a greater bendability than said proximal portion, and comprising a softer plastic material than the material from which the proximal portion is formed;
   a helical wire support member carried by said distal portion only, to provide kink-resistance upon bending of said distal portion and to aid in providing greater bendability than said proximal portion, the helical wire support member defining coils, said proximal portion carrying a tubular braid, said braid being completely embedded within said proximal portion and said helical wire support member being completely embedded within said distal portion.

15. An intravascular catheter as defined by claim 14, in which said helical wire support member is free of wire extending inside of the helix, whereby a clear, open volume is provided within the helix to facilitate passage of PTCA catheters or the like within said helical wire support member.

16. An intravascular catheter as defined by claim 14, in which said distal portion comprises an inner tubular member, said helical wire support member being carried by said inner tubular member and positioned outside of said inner tubular member, and an outer tubular section embedding said helical wire support member therein.

17. The intravascular catheter of claim 14 in which said coils are spaced from each other.

18. An intravascular catheter which comprises:

an elongated tube having a proximal portion and a distal portion;

said proximal portion extending most of the length of the catheter and having a greater torsional stiffness than said distal portion;

said distal portion having a greater bendability than said proximal portion;

a helical wire support member completely embedded within said distal portion only to provide kink-resistance upon bending of said distal portion and to aid in providing greater bendability than said proximal portion, said distal portion, in its natural, unstressed configuration, being curved where said helical wire support member is carried;

said proximal portion carrying a braided wire tubular support member embedded therein.

19. The intravascular catheter of claim 18 in which said distal portion is less than one tenth the length of said proximal portion.

20. The intravascular catheter of claim 18 in which said helical wire support member has coils spaced from each other.

21. The catheter of claim 18 in which said distal portion comprises a plastic material having a shore "D" durometer of 25 to 50, while said proximal portion comprises a stiffer plastic material.

22. The catheter of claim 14 in which the wire of said helical support member defines a rectangular cross section, with the width of said wire being greater than the radial depth thereof.

23. The catheter of claim 22 in which said distal catheter portion carries a distal tip that is free of supporting strands.

24. The catheter of claim 23 in which said distal catheter portion defines a preformed bend.

* * * * *